US006699674B2

(12) United States Patent
Ching et al.

(10) Patent No.: US 6,699,674 B2
(45) Date of Patent: Mar. 2, 2004

(54) EXPRESSION AND REFOLDING OF TRUNCATED RECOMBINANT MAJOR OUTER MEMBRANE PROTEIN ANTIGEN (R56) OF ORIENTIA TSUTSUGAMUSHI AND ITS USE IN ANTIBODY BASED DETECTION ASSAYS AND VACCINES

(75) Inventors: Wei-Me Ching, Bethesda, MD (US); Daryl J. Kelly, Glenn Dale, MD (US); Gregory A. Dasch, Baltimore, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/171,520

(22) Filed: Jun. 14, 2002

(65) Prior Publication Data

US 2003/0185837 A1 Oct. 2, 2003

Related U.S. Application Data

(62) Division of application No. 09/218,425, filed on Dec. 22, 1998, now Pat. No. 6,482,415.

(60) Provisional application No. 60/068,732, filed on Dec. 24, 1997.

(51) Int. Cl.[7] ................................................ G01N 33/53

(52) U.S. Cl. ........................ 435/7.1; 435/7.2; 435/7.32; 435/7.22; 435/7.9; 435/7.92; 435/7.93; 435/7.94; 435/7.95; 530/350

(58) Field of Search .............................. 435/4, 7.1, 7.2, 435/7.32, 7.22, 7.9, 7.92, 7.93, 7.94, 7.95; 530/350

(56) References Cited

U.S. PATENT DOCUMENTS 5,439,808 A * 8/1995 Blake et al.

OTHER PUBLICATIONS

Stover et al. Infect. Immun. 1990. 58(7): 2076–2084.*
Kim et al. J.Clin. Microbiol. 1993. 31(3): 598–605.*
Ohashi et al. Infect. Immun. 1989. 57(5): 1427–1431.*
Ohashi et al. Microbiol. Immunol. 1988. 31(11): 1085–1092.*

* cited by examiner

*Primary Examiner*—Jennifer Graser
(74) *Attorney, Agent, or Firm*—Joseph K. Hemby, Jr.; A. David Spevack

(57) ABSTRACT

A recombinant, refolded non-fusion polypeptide expressed from a truncated r56 gene of the causative agent of scrub typhus, *Orientia tsutsugamushi*. The invention is useful for detecting prior exposure to scrub typhus and as a component in vaccine formulations.

14 Claims, 7 Drawing Sheets

SEQUENCE LISTING

```
<160> NUMBER OF SEQ ID NOS: 3

<210> SEQ ID NO 1
<211> LENGTH: 378
<212> TYPE: PRT
<213> ORGANISM: Orientia Tsutsugamushi

<400> SEQUENCE: 1

Met Thr Ile Ala Pro Gly Phe Arg Ala Glu Ile Gly Val Met Tyr Leu
  1               5                  10                  15

Thr Asn Ile Thr Ala Gln Val Glu Glu Gly Lys Val Lys Ala Asp Ser
             20                  25                  30

Val Gly Glu Thr Lys Ala Asp Ser Val Gly Gly Lys Asp Ala Pro Ile
         35                  40                  45

Arg Lys Arg Phe Lys Leu Thr Pro Pro Gln Pro Thr Ile Met Pro Ile
     50                  55                  60

Ser Ile Ala Val Arg Asp Phe Gly Ile Asp Ile Pro Asn Ile Pro Gln
 65                  70                  75                  80

Gln Gln Ala Gln Ala Ala Gln Pro Gln Leu Asn Asp Glu Gln Arg Ala
                 85                  90                  95

Ala Ala Arg Ile Ala Trp Leu Lys Asn Cys Ala Gly Ile Asp Tyr Arg
            100                 105                 110

Val Lys Asn Pro Asn Asp Pro Asn Gly Pro Met Val Ile Asn Pro Ile
        115                 120                 125

Leu Leu Asn Ile Pro Gln Gly Asn Pro Asn Pro Val Gly Asn Pro Pro
    130                 135                 140
```

-continued

```
Gln Pro Arg Ala Asn Pro Pro Ala Gly Phe Ala Ile His Asn His Glu
145                 150                 155                 160

Gln Trp Arg His Leu Val Val Gly Leu Ala Ala Leu Ser Asn Ala Asn
                165                 170                 175

Lys Pro Ser Ala Ser Pro Val Lys Val Leu Ser Asp Lys Ile Thr Gln
            180                 185                 190

Ile Tyr Ser Asp Ile Lys His Leu Ala Asp Ile Ala Gly Ile Asp Val
        195                 200                 205

Pro Asp Thr Ser Leu Pro Asn Ser Ala Ser Val Glu Gln Ile Gln Asn
    210                 215                 220

Lys Met Gln Glu Leu Asn Asp Leu Leu Glu Glu Leu Arg Glu Ser Phe
225                 230                 235                 240

Asp Gly Tyr Leu Gly Gly Asn Ala Phe Ala Asn Gln Ile Gln Leu Asn
                245                 250                 255

Phe Val Met Pro Gln Gln Ala Gln Gln Gln Gly Gln Gly Gln Gln Gln
            260                 265                 270

Gln Ala Gln Ala Thr Ala Gln Glu Ala Val Ala Ala Ala Ala Val Arg
        275                 280                 285

Leu Leu Asn Gly Asn Asp Gln Ile Ala Gln Leu Tyr Lys Asp Leu Val
    290                 295                 300

Lys Leu Gln Arg His Ala Gly Ile Lys Lys Ala Met Glu Lys Leu Ala
305                 310                 315                 320

Ala Gln Gln Glu Glu Asp Ala Lys Asn Gln Gly Glu Gly Asp Cys Lys
                325                 330                 335

Gln Gln Gln Gly Thr Ser Glu Lys Ser Lys Lys Gly Lys Asp Lys Glu
            340                 345                 350

Ala Glu Phe Asp Leu Ser Met Ile Val Gly Gln Val Lys Leu Tyr Ala
        355                 360                 365

Asp Val Met Ile Thr Glu Ser Val Ser Ile
    370                 375


<210> SEQ ID NO 2
<211> LENGTH: 36
<212> TYPE: DNA
<213> ORGANISM: Orientia Tsutsugamushi

<400> SEQUENCE: 2

ttggctgcac atatgacaat cgctccagga tttaga                                36


<210> SEQ ID NO 3
<211> LENGTH: 48
<212> TYPE: DNA
<213> ORGANISM: Orientia Tsutsugamushi

<400> SEQUENCE: 3

ctttctagaa gtataagcta acccggatcc aacaccagcc tatattga                   48
```

EXPRESSION AND REFOLDING OF TRUNCATED RECOMBINANT MAJOR OUTER MEMBRANE PROTEIN ANTIGEN (R56) OF ORIENTIA TSUTSUGAMUSHI AND ITS USE IN ANTIBODY BASED DETECTION ASSAYS AND VACCINES

This application is a divisional application of U.S. patent application Ser. No. 09/218,425 Dec. 22, 1998, now U.S. Pat. No. 6,482,415, which claims the benefit of 60/068,732 Dec. 24, 1997.

BACKGROUND OF THE INVENTION

1. Field of the Invention

This invention relates to detecting exposure to microorganisms by the use of serodiagnostic assays, and more specifically to detecting exposure to *Orientia tsutsugamushi.*

2. Description of Prior Art

Scrub typhus or tsutsugamushi disease is an acute, febrile disease caused by infection with *Orientia* (formerly Rickettsia) *tsutsugamushi*. It accounts for up to 23% of all febrile episodes in endemic areas of the Asia-Pacific region (5). The incidence of disease has increased in some countries during the past several years (6).

*O. tsutsugamushi* is a gram negative bacterium, but in contrast to other gram negative bacteria, *O. tsutsugamushi* has neither lipopoly-saccharide nor a peptidoglycan layer (1) and the ultrastructure of its cell wall differs significantly from those of its closest relatives, the typhus and spotted fever group species in the genus Rickettsia (33). The major surface protein antigen of *O. tsutsugamushi* is the variable 56 kDa protein which accounts for 10–15% of its total protein (16, 28). Most type-specific monoclonal antibodies to Orientia react with homologues of the 56 kDa protein (16, 24, 42). Sera from most patients with scrub typhus recognize this protein, suggesting that it is a good candidate for use as a diagnostic antigen (28).

Diagnosis of scrub typhus is generally based on the clinical presentation and the history of a patient. However, differentiating scrub typhus from other acute tropical febrile illnesses such as leptospirosis, murine typhus, malaria, dengue fever, and viral hemorrhagic fevers can be difficult because of the similarities in signs and symptoms. Highly sensitive polymerase chain reaction (PCR) methods have made it possible to detect *O. tsutsugamushi* at the onset of illness when antibody titers are not high enough to be detected (14, 19, 36). PCR amplification of the 56 kDa protein gene has been demonstrated to be a reliable diagnostic method for scrub typhus (14, 18). Furthermore, different genotypes associated with different Orientia serotypes could be identified by analysis of variable regions of this gene without isolation of the organism (14, 17, 18, 25, 39). However, gene amplification requires sophisticated instrumentation and reagents generally not available in most rural medical facilities. Current serodiagnostic assays such as the indirect immunoperoxidase (IIP) test and the indirect immunofluorescent antibody (IFA) or microimmunofluorescent antibody (MIF) tests require the propagation of rickettsiae in infected yolk sacs of embryonated chicken eggs or antibiotic free cell cultures (4, 20, 30, 43).

At the present time the only commercially available dot-blot immunologic assay kits (Dip-S-Ticks) requires tissue culture grown, Renografin density gradient purified, whole cell antigen (41). Only a few specialized laboratories have the ability to culture and purify *O. tsutsugamushi* since this requires biosafety level 3 (BL3) facilities and practices.

The availability of recombinant rickettsial protein antigens which can be produced and purified in large amounts and have similar sensitivity and specificity to rickettsia-derived antigens would greatly reduce the cost, transport, and reproducibility problems presently associated with diagnostic tests which require the growth and purification of rickettsiae.

Recently, a recombinant 56 kDa protein from Boryong strain fused with maltose binding protein was shown to be suitable for diagnosis of scrub typhus in a enzyme-linked immunosorbent assay (ELISA) and passive hemagglutination test (21, 22). Although this protein overcomes some of the above-described disadvantages, it still has certain inherent disadvantages as an assay reagent because it is a fusion protein.

SUMMARY OF THE INVENTION

Accordingly, an object of this invention is a recombinant construct and expressed polypeptide possessing immunogenic regions.

Another object of the invention is a recombinant polypeptide encoding a portion of the 56 kDa protein of *O. tsutsugamushi* encoded by amino acids 80 to 456.

A still further object of the invention is a recombinant truncated 56 kDa polypeptide which is re-folded to give a soluble moiety.

An additional object of this invention is the use of the recombinant polypeptide in antibody based assays for improved methods for the detection of *O. tsustugamushi* exposure, in research and in clinical samples.

Yet another object of the invention the expression of the truncated r56 in different host backgrounds of bacterial strains for use in different vaccine formulations against scrub typhus infection.

These and other objects, features and advantages of the present invention are described in or are apparent from the following detailed description of preferred embodiments.

BRIEF DESCRIPTION OF THE DRAWINGS

The invention will be described with reference to the drawings, in which like elements have been denoted throughout by like reference numerals. The representation in each of the figures is diagrammatic and no attempt is made to indicate actual scales or precise ratios. Proportional relationships are shown as approximations.

DETAILED DESCRIPTION

There is a critical need for rapid, assays for the determination of exposure to *Orientia tsutsugamushi*, the causitive agent of scrub typhus. Currently available assays require bacterial antigen which must be purified by extremely labor intensive methods after first propagating the organism in specialized laboratories (BSL-3). Furthermore, there is currently no efficacious vaccine for scrub.

Recombinantly produced proteins, which are specific to *O. tsutsugamushi* and recognized by specific antibodies would greatly facilitate the practical use of anti-scrub typhus assays since the protein can be produced more economically and with higher purity compared to material from whole bacteria. Additionally, recombinant polypeptides can be used in sub-unit vaccines.

The 56 kDa protein of *O. tsutsugamushi* is extremely abundant in the bacteria and is highly immunogenic. Although the use of recombinant 56 kDa protein from *O. tsutsugamushi* has been reported, it was produced as a fusion peptide which creates a number of inherent disadvantages, including reduced immunogenicity due to improper folding of the bacteria polypeptide. To overcome these problems a non-fusion, recombinant poly-peptide from 56 kDa protein was produced. Furthermore, in order to ensure proper folding of the polypeptide after translation, and therefore enhanced immune recognition, a truncated recombinant 56 kDa gene was created with the truncation created at specific points (Seq ID No. 1). The truncated 56 kDa gene is then expressed using efficient expression systems. This truncated, recombinant polypeptide is then use as antigen in antibody based assays and to induce an immune response against scrub typhus.

EXAMPLE 1

Cloning and Expression of Recombinant 56 kDa Gene.

Figure 1:
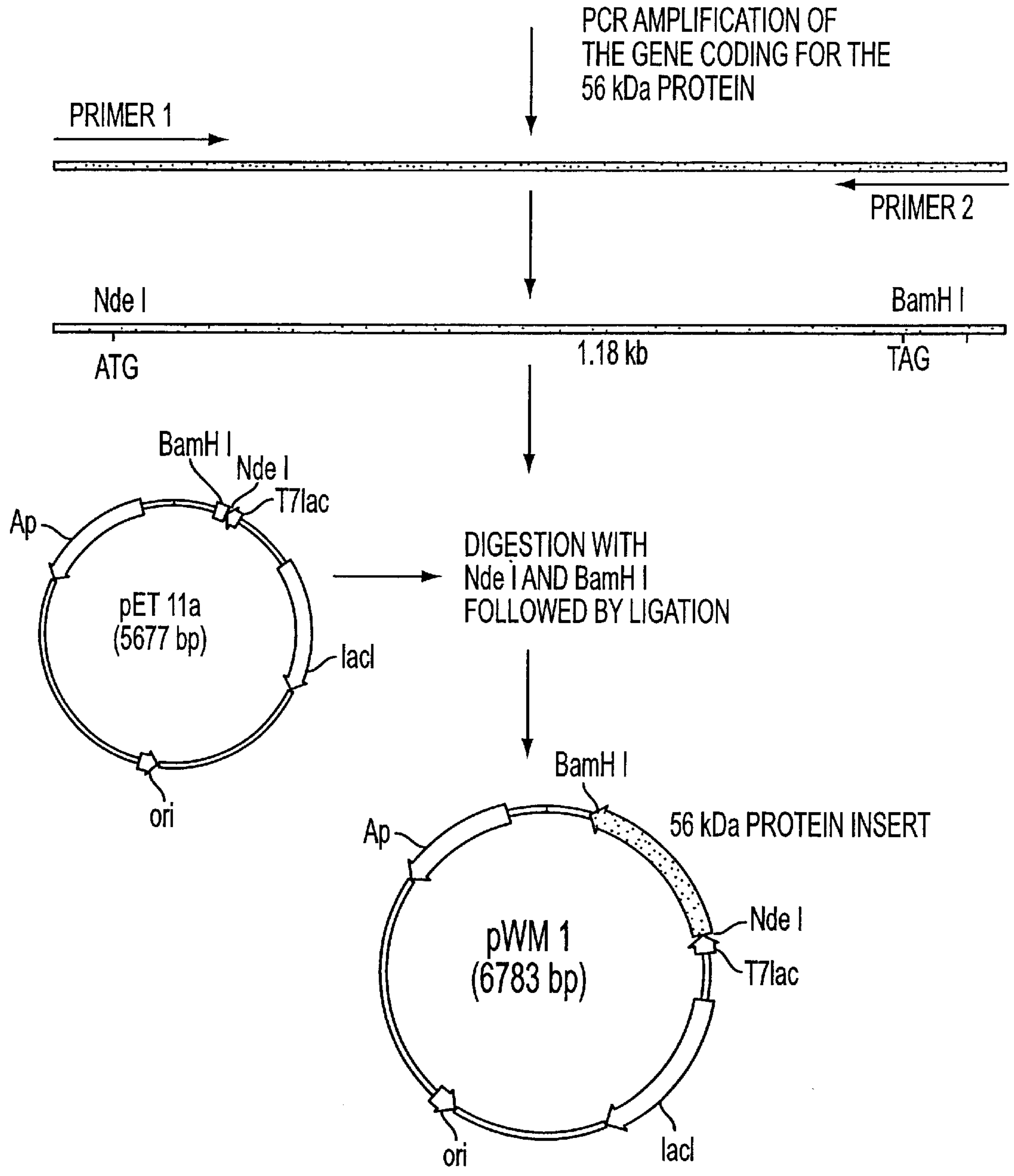
FIG. 1 shows the strategy for cloning and construction of pWM1 that expresses the truncated recombinant 56 kDa protein antigen from *O. tsutsugamushi* Karp strain.

As shown in FIG. 1, a primer pair (56F(226/261), 5'-TTGGCTGCACATATGACAATCGCTCCAGGAT TTAGA-3' (Seq. ID No. 2) and 56R(1409/1363), 5'-CTTTCTAGAAGTATAAGCTAACCC GGATCCAACACCAGCCTATATTGA-3' (Seq. ID No. 3) was designed using the nucleotide sequence of the open reading frame for the Karp 56 kDa protein (34). The respective restriction sites for Nde I and BamH I are underlined and the new initiation codon and reverse complement of the new stop codon are shown in bold and italic, respectively. The forward primer 56F(226/261) contained the methionine initiation codon, at residue 80, which is part of the Nde I recognition sequence. The reverse primer 56R(1409/1363) created an alteration of the tyrosine codon at residue 457 to a stop codon and contained a BamH I site. The coding sequence from amino acid 80 to 456 was amplified by polymerase chain reaction (PCR), using the above primers, from DNA isolated from plaque-purified *O. tsutsugamushi* Karp strain grown in irradiated L929 cells (18). The truncated 56 kDa gene was amplified in a mixture of 400 mM each of deoxynucleotide triphosphate, 1 mM of each primer, 1.5 U of Taq polymerase (Perkin-Elmer, CA) in 10 mM Tris-HCl buffer, pH 8.3, 1.5 mM $MgCl^2$, and 50 mM KCl. The PCR reaction was started with 15 sec at 80° C., 4 min at 94° C., and followed by 30 cycles of 94° C. for 1 min, 57° C. for 2 min and 72° C. for 2 min. The last cycle was extended for 7 min at 72° C. The amplified fragment (1.18 kb) was digested with Nde I (BioLab, MA) and BamH I (Life Technology, MD) and ligated with doubly digested expression vector. Any plasmid or viral expression system can be used as long as polypeptide is expressed. The preferred expression system is the plasmid system pET11a (Novagen, WI)(FIG. 1) to yield the expression system pWM1. The *E. coli* strain HB101 was transformed with the ligation mixture and colonies screened for inserts with the right size and orientation.

Expressed r56 is constructed such that the N-terminal 79 residues or the C-terminal 77 residues of the intact 56 kDa protein, as deduced from the open reading frame of its encoding gene, is not present. Both regions deleted were predicted to be relatively hyrophobic and be responsible for association with the rickettsial outer membrane. Truncation of these termini facilitate the refolding of the expressed polypeptide and favors solubility its solubility in aqueous solutions and simplification of handling.

Purification of the 56 kDa Protein.

Figure 2:
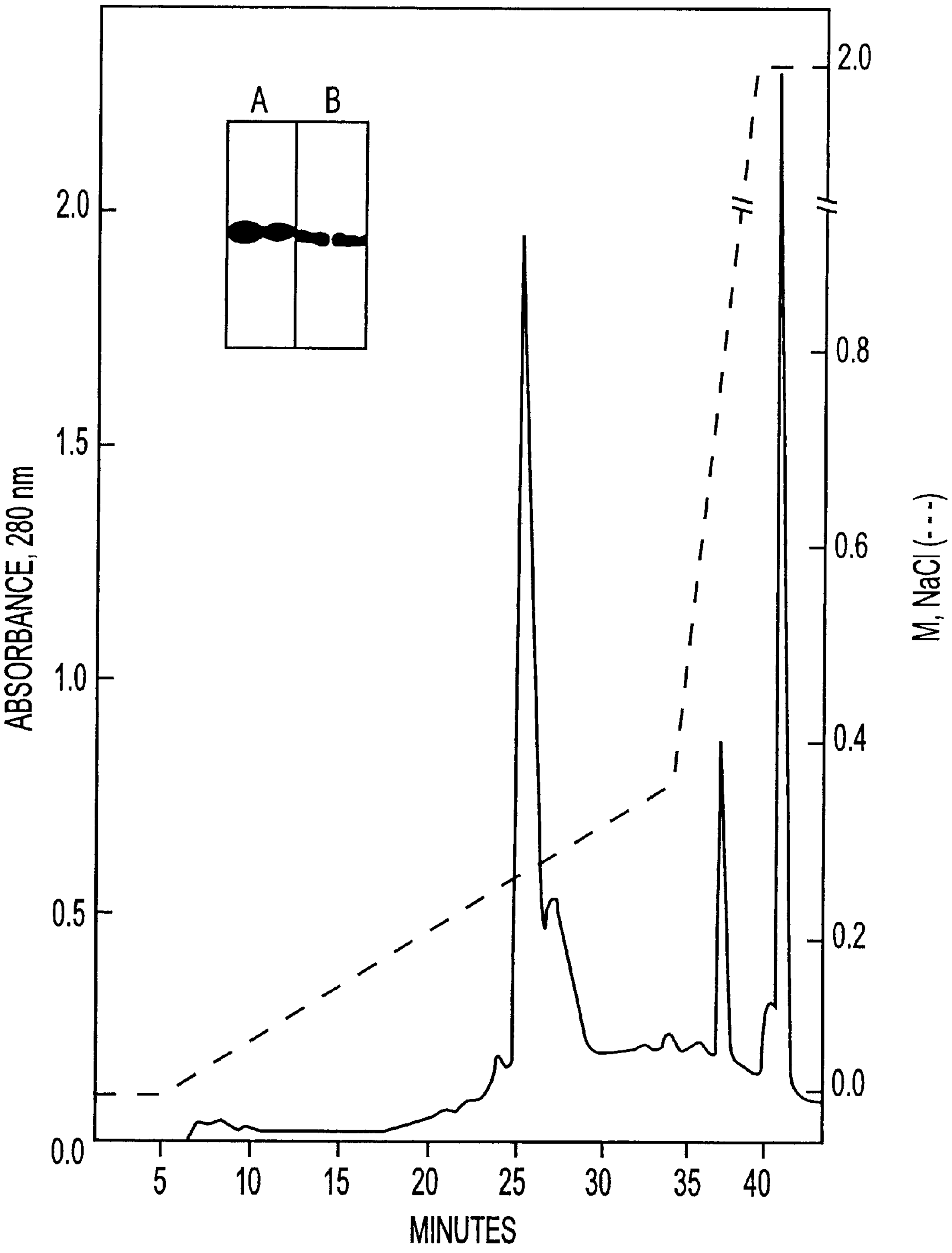
FIG. 2 shows the HPLC ion exchange profile for the purification of r56. The insert shows the Coomassie blue staining (A) and Western blot analysis (B) of the two peak fractions at 25 (left lane) and 27 min (right lane) which contain most of the r56.

Plasmids carrying the insert of the truncated and amplified 56 kDa gene are transformed into the expression host *E. coli* BL21. The optimum time and IPTG concentration for r56 expression is determined. Recombinant *E. coli* expressing r56 are grown overnight at 37° C. with shaking. Cell pellets from 100 ml cultures are resuspended in 3 ml of buffer A (20 mM Tris-HCl, pH 8.0), containing 5 mM EDTA and 1 mM PMSF. Ultrasonic disruption of the cell is performed with cooling on ice. Disrupted cell extract is centrifuged at 8,000× g for 30 min. The pellets are vortexed to a homogeneous suspension with 2 M urea in buffer A, placed on a shaker at room temperature for an additional 10 min, centrifuged for 5 min at 14,000 rpm in an Eppendorf centrifuge (model 5415). The entire process is then repeated with 4 M urea in buffer A. Finally the pellets are dissolved in 8 M urea in buffer A and applied onto an HPLC ion exchange (DEAE) column (Waters, 0.75 cm×7.5 cm) for fractionation. Proteins are eluted with a linear gradient of buffer B and buffer C (6 M urea and 2 M NaCl in buffer A) from 0.0 to 0.4 M NaCl over 30 min at a flow rate of 0.5 ml/min. Fractions are collected, typically at one min per fraction. For a typical run, approximately 200 μl of extract obtained from a total of 10 ml culture is loaded onto the column (FIG. 2). The presence of r56 in fractions was detected by dot-blot immunoassay. Positive fractions with significant amounts of protein, presumably containing expressions of the truncated and amplified 56 kDa gene, are also analyzed by SDS-PAGE and Western blotting.

Testing for Polypeptide Expression by Dot-Blot Immunoassay.

Fractions collected from HPLC are screened for r56 polypeptide by dot-blot assay. A 2 μl sample of each eluted fraction is diluted into 200 μl of water and applied to a well of a 96-well dotblotter (Schleicher and Schuell). After drying under vacuum for 5 min, the nitrocellulose membrane is blocked with 5% nonfat milk for 30 min, then incubated with monoclonal antibody Kp56c specific for Karp 56 kDa protein antigen (23) for one hr, washed 4 times with phosphate buffer saline (PBS) 5 min each time, and incubated with peroxidase conjugated goat anti-mouse IgG (H+L) (Bio-Rad Laboratories) for 30 min. After washing with PBS 5 times for 5 min, substrate solution containing 5:5:1 ratio of TMB peroxidase substrate, hydrogen peroxide solution, and TMB membrane enhancer (Kirkegaard and Perry Laboratories) is added onto the nitrocellulose membrane. The enzymatic reaction is stopped after 2 min by washing the membrane in distilled water. The above-described test can be incorporated into any dot-blot, spot or dipstick type test structure. These structures are extensively described in the prior art.

Confirmation of Polypeptide Identity.

Confirmation of the identity of the polypeptide is confirmed by amino acid sequence analysis of SDS-PAGE purified, CNBr cleaved fragments of the peak fractions (7). The sequences are identical to that deduced from nucleotide.

Refolding of r56.

HPLC fractions, in 6M urea, containing peak r56 polypeptide are pooled and sequentially dialyzed against 4 M urea and 2 M urea in buffer A and finally with buffer A only. The final dialysis is against buffer A with two initial changes of buffer for 30 min each, and finally overnight at 4° C. r56 is properly folded since the polypeptide remains soluble in buffer A with no urea present.

Circular Dichroism (CD) Spectrum of r56.

The circular dichroism spectrum of refolded r56 was measured on a JASCO model 715 in Dr. Ettore Apella=s laboratory in NIH, Bethesda, Md. Data were analyzed by Dr. Latchezar I. Tsonev, Henry Jackson Foundation, Rockville, Md., at a protein concentration of 117 μg/ml in 20 mM TrisHCl, pH 8.0 and the calculated molecular weight of 40,903 dalton.

Figure 3:
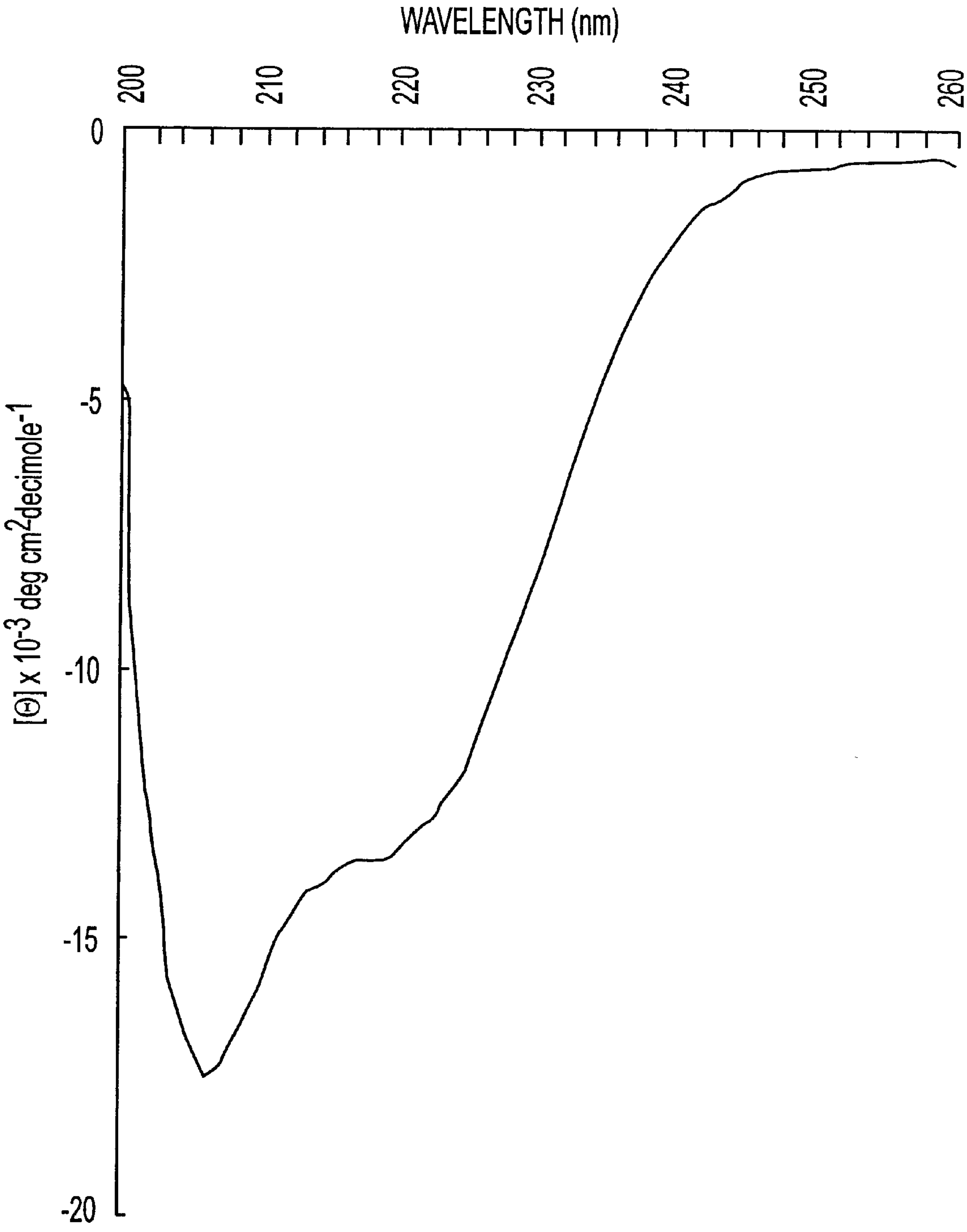
FIG. 3 shows the circular dichroism spectrum of refolded r56.

The CD spectrum of the refolded polypeptide shows that the secondary structure is approximately 38% α-helical, 13% β-sheet and 50% random coil (15)(FIG. 3). This experimental data is similar to that predicted by correctly folded, truncated 56 kDa protein, based on amino acid sequence from nucleic acid sequence (34).

EXAMPLE 2

Use of r56 Polypeptide in Antibody Based Identification Assays.

ELISA Assay Method

The microtiter plates are coated with antigens diluted in PBS overnight at 4° C. and blocked with 0.5% boiled casein for 1 hr, rinsed with PBS twice, 5 min each time. Patient sera are diluted 1:400 with 20 μg/ml of control protein extracts purified from *E. coli* BL21 using a procedure identical to that used for purifying r56 (fractions 21–32 pooled from gradients equivalent to FIG. 2), pre-absorbed for about 1 hr at room temperature, and then added to the ELISA plates. The plates are incubated for 1 hr at room temperature, washed four times with 0.1% Triton X-100 in PBS. Peroxidase conjugated mouse anti-human IgG (Fc specific) (Accurate) diluted 1:8000 and goat anti human IgM (μ chain specific) (Kirkegaard & Perry) are then added. After 1 hr incubation at room temperature, the plates are washed four times with 0.1% Triton X-100 in PBS and the last wash is with PBS only before the addition of substrate ABTS (Kirkegaard & Perry). The ODs at 405 nm are read after 15 min incubation at room temperature. Rabbit sera were diluted 1:250 with PBS only. All procedures are the same as for detection of human antibodies except that rabbit sera is not preabsorbed with protein preparations from BL21 and peroxidase conjugated goat anti-rabbit IgG (Kirkegaard & Perry) diluted 1:2,000 is used.

Figure 4:
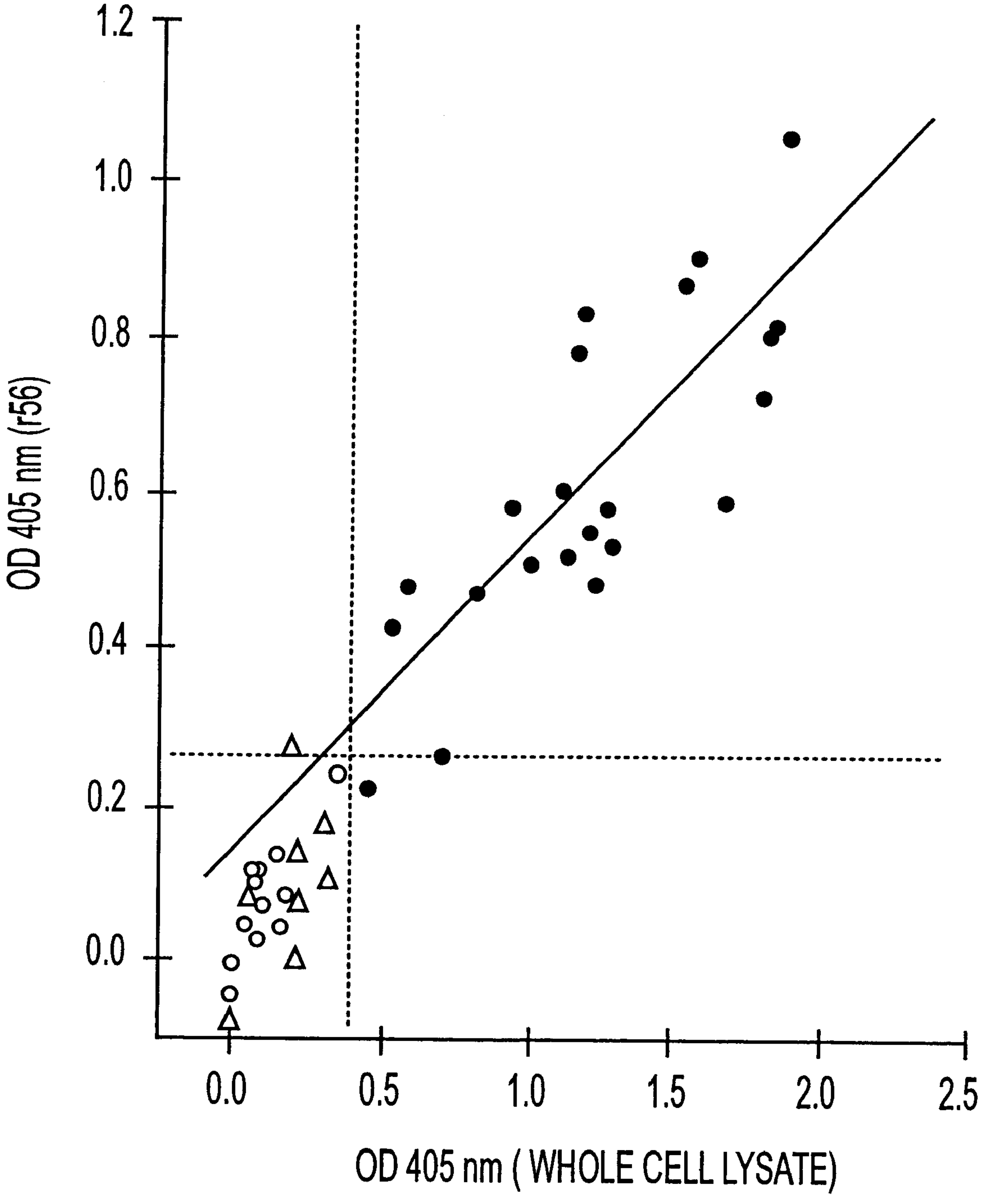
FIG. 4 shows a comparison of ELISA IgG reactivity of r56 and *O. tsutsugamushi* Karp strain whole cell lysate with rabbit antisera (see Table 1).

The recombinant r56 polypeptide contains only a portion of the 56 kDa protein, the major antigen that is used to differentiate antigenic types of Orientia. In addition rickettsial whole cell lysate contains numerous other protein antigens besides intact 56 kDa antigen. A comparison of ELISA IgG reactivity of r56 and *O. tsutsugamushi* Karp strain whole cell lysate with rabbit antisera is shown (FIG. 4). The dotted lines represent the mean+2 standard deviations of reactivity of the normal rabbit sera. The solid line is the linear regression of the data for the 22 anti-Orientia rabbit sera tested (r=0.81). Eight control normal rabbit sera (open diamonds); five antisera against non-rickettsial antigens (open triangles): eight antisera to Rickettsiales other than Orientia (open squares); and 22 antisera to eight antigen prototypes of *O. tsutsugamushi* (solid circles) are compared. Positive breakpoints (mean+2SD) for reactivity of both r56 and whole cell Orientia lysate (WCEX) and standard ELISA using eight normal rabbit (ODs of 0.27 and 0.38), respectively, are established. (FIG. 4, Table 1). None of the eight rabbits immunized with other species of Rickettsiales or the five antisera prepared against either L-cell, yolk sac, or *E. coli* exhibit reactivity higher than the cutoff for WCEX while one rabbit antiserum against primary chick embryo reacted barely above the breakpoint with r56 (OD of 0.28) (FIG. 4, Table 1). On the other hand 20 of 22 rabbit antisera against the eight Orientia antigenic prototypes react slightly above the breakpoint with r56 and all sera exhibit positive ELISA with WCex (FIG. 4, Table 1). Although the r56 antigen exhibits lower ELISA reactivity at the amount employed than that obtained with WCex, the Orientia rabbit antisera exhibit a very good correlation of ELISA reactions to the two antigens (r=0.8, n=22). One Kato antiserum and one TA686 antiserum which exhibit relatively low positive ELISA reactivity with WCex does not react, significantly, with r56 antigen (Table 1). Consequently, the ELISA with folded r56 gives equivalent results as the standard ELISA in the detection of Orientia-specific antibodies by ELISA (specificity-92.3%, sensitivity-90.9%, accuracy-91.4%) with WCEX ELISA as the reference assay) even though r56 is only a truncated portion of one of the complex antigens found in WCex.

TABLE 1

Comparison of ELISA reactivity of purified Karp whole cell lysate and folded r56 with rabbit antisera.

| Antisera against different antigens | ELISA ODs (405 nm) of whole cell lysate (corresponding r56 result) |
|---|---|
| *O. tsutsugamushi* strain | |
| Karp | 0.94 (0.58), 1.87 (1.04), 1.81 (0.80), 1.83 (0.81) |
| Kato | 0.46 (0.22), 1.02 (0.50), 1.16 (0.77), 1.27 (0.58) |
| Gilliam | 0.54 (0.42), 1.20 (0.54) |
| TH1817 | 1.67 (0.59), 1.12 (0.60), 1.29 (0.53), 0.83 (0.47) |
| TA678 | 0.59 (0.48) |
| TA686 | 0.71 (0.26), 1.52 (0.86) |
| TA716 | 1.24 (0.48), 1.14 (0.51) |
| TA763 | 1.79 (0.72), 1.57 (0.89), 1.18 (0.82) |
| Other Rickettsiales | |
| *R. prowazekii* | 0.08 (0.12) |
| *R. typhi* | 0.18 (0.08) |
| *R. rickettsii* | 0.06 (0.04), 0.15 (0.14) |
| *R. conorii* | 0.10 (0.11), 0.07 (0.11) |
| *E. sennetsu* | 0.01 (0.05) |
| *E. risticii* | 0.01 (−0.01) |
| Non rickettsial antigens | |
| Yolk sac | 0.22 (0.08) |
| L929-cell | 0.01 (−0.08) |
| Primary chick embryo | 0.20 (0.28) |
| RAW 264.7 cells | 0.22 (0.14) |
| *E. coli* HB101 | 0.32 (0.11) |
| No antigen control (n = 8) | 0.135 + 0.123 (0.093 + 0.088) |

[a]OD values listed are the difference between data with antigen and without antigen.

Comparison of r56 ELISA with IIP Test with Human Sera.

Figure 5:
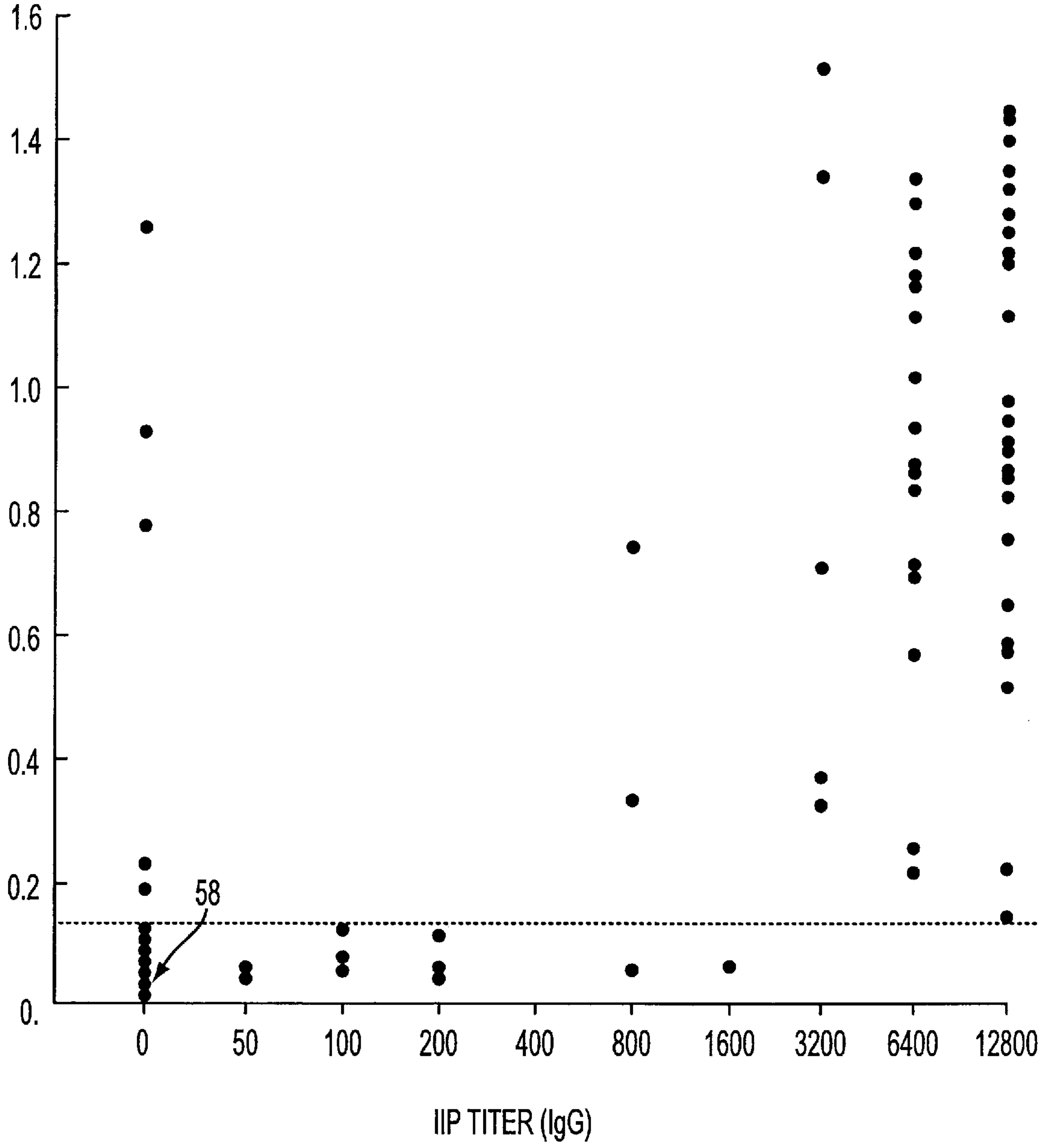
FIG. 5 shows a scattergram of IgG ELISA reactivity of 128 Thai patient sera obtained with folded r56 and the corresponding IIP test IgG titers.
Figure 6:
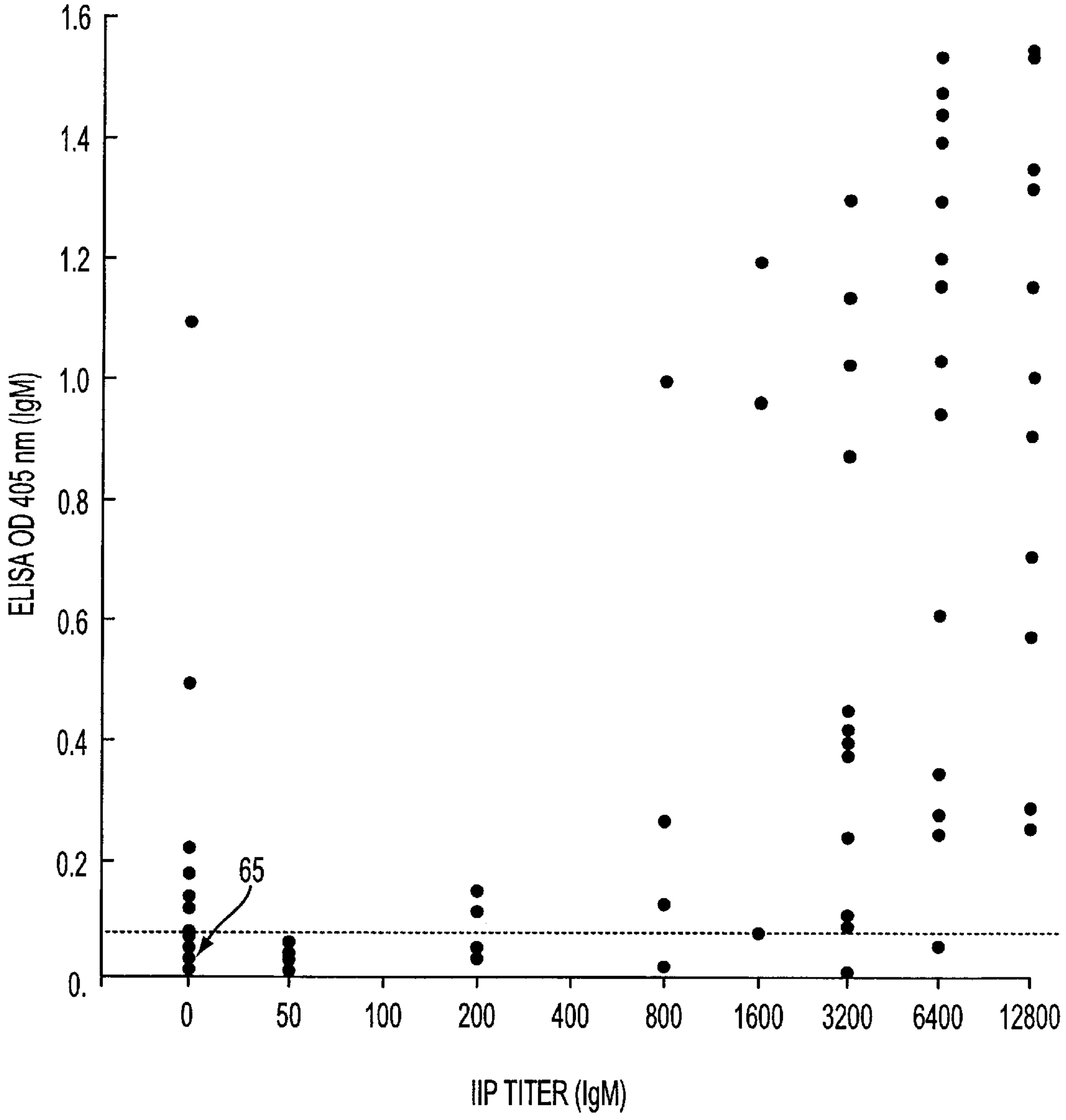
FIG. 6 shows a scattergram of IgM ELISA reactivity of 128 Thai patient sera obtained with folded r56 and the corresponding IIP test IgM titers.

Seventy-four sera from healthy Thai soldiers were used to establish an ELISA break point for positive reactions (mean+2 SD) with r56 as antigen. These are 0.05+0.06=0.11 OD for IgG, and 0.032+0.032=0.064 OD for IgM at 1:400 serum dilution. The r56 ELISA ODs of 128 sera from patients suspected of scrub typhus from Korat, Thailand were compared with the IgG and IgM titers determined by an IIP method using a mixture of intact Karp, Kato, and Gilliam prototypes of Orientia. The IIP method used was described previously (20, 38) (FIGS. 5 and 6). Using IIP titers as the gold standard, the sensitivity, specificity, and accuracy values of ELISA results with the 128 test sera are calculated using different positive breakpoints for the IIP test (Table 2).

TABLE 2

Comparison of efficiency of r56 ELISA with the indirect immunoperoxidase assay (IIP) for 128 Thai patient sera.

| Titer | Ig | No. pos. sera by IIP | ELISA % Sensitivity | ELISA % Specificity | ELISA % Accuracy |
|---|---|---|---|---|---|
| 1:50 | IgG | 68 | 82% | 92% | 87% |
| | IgM | 56 | 91% | 92% | 91% |
| 1:200 | IgG | 61 | 92% | 93% | 92% |
| | IgM | 52 | 98% | 92% | 95% |
| 1:400 | IgG | 57 | 90% | 93% | 95% |
| | IgM | 47 | 100% | 93% | 93% |

Figure 7:
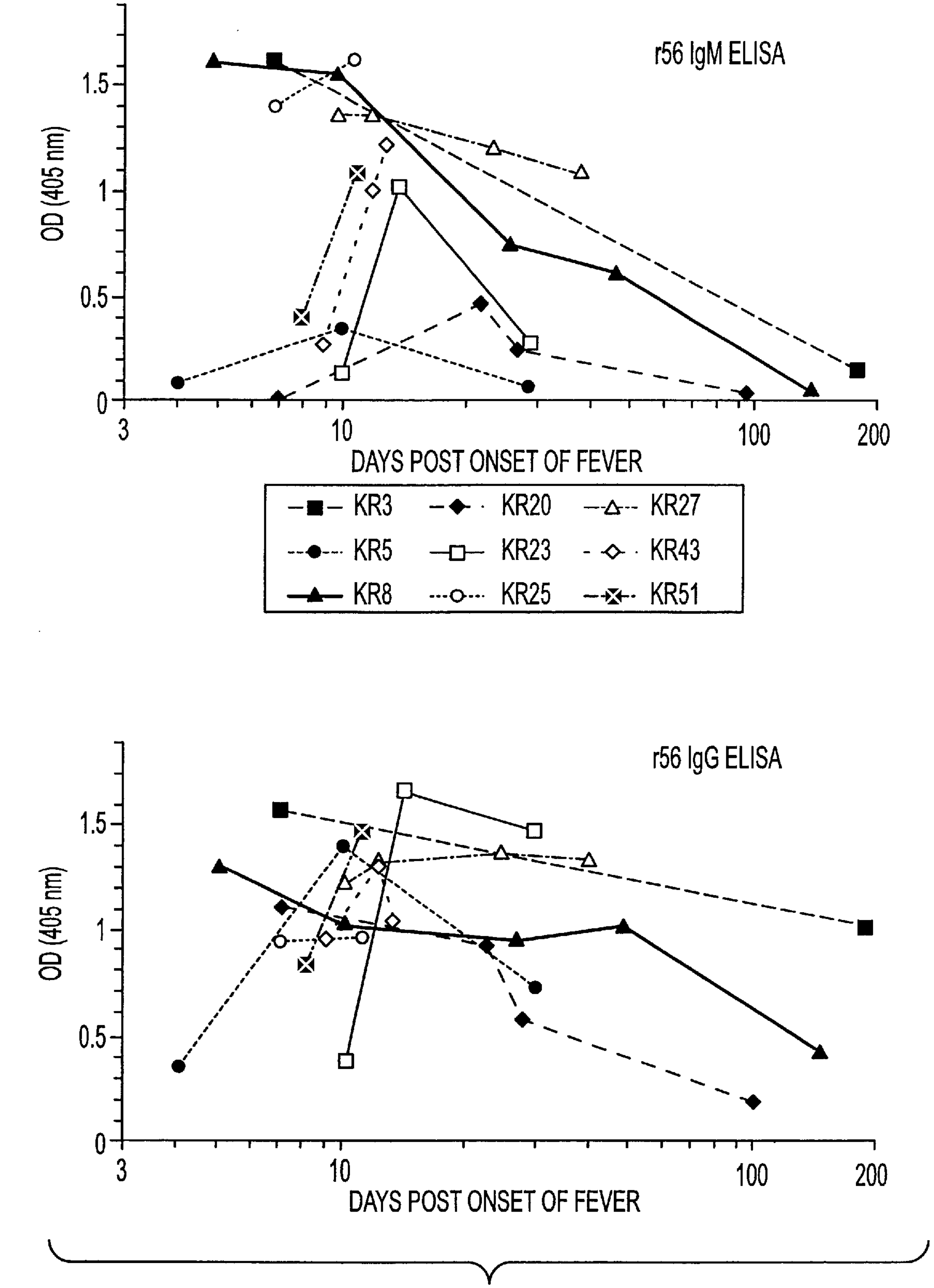
FIG. 7 shows the time course of IgM and IgG reactivity of confirmed cases of scrub typhus by ELISA with folded r56 as antigen.

Sera from 13 isolate and PCR-confirmed cases of scrub typhus were analyzed to characterize the kinetics and magnitude of the IgM and IgG immune responses as measured by IIP test titers and by r56 ELISA ODs. Representative data are shown in FIG. 7 and Table 3. Four sera from 4 different cases were available from the first week after onset of fever (days 4–7). All are positive by IIP for both IgM and IgG with titers between 3200 and 12,800 for all cases. In contrast, by ELISA, KR5 (day 4, Table 3) has very low IgM and IgG ODs and KR20 is negative for IgM even at day 7 while the other two sera (KR8, KR25) are more reactive by IgM assay than IgG. Sixteen sera from 12 cases were collected 8–14 days post onset of fever. By IIP both IgM and IgG titers are again high and within one two-fold dilution for all of these sera except the day 10 serum from KR23 which also has the lowest IgM and IgG ELISA OD's (Table 3, FIG. 7). Except for three other sera from days 8–10 (KR5, KR43, KR51) which also had low IgM ODs, most sera has similar IgG and IgM ELISA reactions. Five sera from four cases were obtained in weeks 3–4 after infection. Two of the cases (KR8, KR20) exhibit a decrease in IgM ODs by ELISA at this time point which are not apparent by IIP assay while the other reactions all remain strong. In weeks 5–6 after infection two of 5 sera from different patients decline in IIP IgM titers (but not IgG titers) while three sera decline significantly in ELISA IgM and one by ELISA IgG. In striking contrast, KR27 maintain high levels of specific antibody as measured by all assays from 10 to 39 days (Table 3). With all six sera collected from six different cases 95–202 days post onset of illness, IgM IIP titers and both IgM and IgG ELISA ODs drop significantly; in contrast, only one of the sera exhibit a decline in IgG IIP titers (FIG. 7).

TABLE 3

Comparison of IIP test titers with ELISA r56 OD's obtained with human sera from confirmed cases of scrub typhus.

| Patient | Days post Onset of fever | IIP Test Titer IgM | IIP Test Titer IgG | r56 ELISA (OD) IgM | r56 ELISA (OD) IgG |
|---|---|---|---|---|---|
| KR5 | 4 | 3,200 | 3,200 | 0.10 | 0.31 |
| KR5 | 10 | 6,400 | 12,800 | 0.34 | 1.26 |
| KR5 | 29 | 1,600 | 12,800 | 0.07 | 0.63 |
| KR8 | 5 | 12,800 | 12,800 | 1.55 | 1.18 |
| KR8 | 10 | 6,400 | 6,400 | 1.48 | 0.92 |
| KR8 | 26 | 12,800 | 12,800 | 0.71 | 0.85 |
| KR8 | 47 | 12,800 | 12,800 | 0.57 | 0.90 |
| KR8 | 137 | 50 | 3,200 | 0.05 | 0.35 |
| KR10 | 10 | 12,800 | 6,400 | 1.30 | 1.15 |
| KR10 | 201 | 200 | 6,400 | 0.053 | 0.20 |
| KR20 | 7 | 3,200 | 6,400 | 0.01 | 1.00 |
| KR20 | 22 | 3,200 | 6,400 | 0.44 | 0.82 |
| KR20 | 27 | 6,400 | 12,800 | 0.24 | 0.50 |
| KR20 | 95 | 200 | 6,400 | 0.03 | 0.13 |
| KR23 | 10 | 200 | 800 | 0.14 | 0.32 |
| KR23 | 14 | 1,600 | 3,200 | 0.97 | 1.50 |
| KR23 | 29 | 800 | 3,200 | 0.26 | 1.32 |
| KR25 | 7 | 12,800 | 12,800 | 1.34 | 0.84 |
| KR25 | 11 | 6,400 | 6,400 | 1.54 | 0.86 |
| KR27 | 10 | 3,200 | 6,400 | 1.30 | 1.10 |
| KR27 | 12 | 6,400 | 12,800 | 1.30 | 1.20 |
| KR27 | 24 | 3,200 | 12,800 | 1.14 | 1.23 |
| KR27 | 39 | 3,200 | 12,800 | 1.03 | 1.20 |
| KR43 | 9 | 6,400 | 6,400 | 0.27 | 0.85 |
| KR43 | 12 | 6,400 | 6,400 | 0.96 | 1.17 |
| KR43 | 13 | 12,800 | 12,800 | 1.16 | 0.93 |
| KR51 | 8 | 3,200 | 12,800 | 0.39 | 0.74 |
| KR51 | 11 | 6,400 | 6,400 | 1.04 | 1.32 |

The excellent sensitivity and specificity of the r56 ELISA in comparison with those of the IIP assay suggest that one protein antigen, i.e. truncated r56, is sufficient for detecting anti-Orientia antibody in sera from patients with scrub typhus. Use of a single moiety in recombinant form improves efficiency of the assay and will reduce cost per assay, significantly.

EXAMPLE 4

Induction of Protective Immune Response.

Because of the significant antibody response exhibited prior to exposure with *O. tsutsugamushi* in rabbits and humans, and the excellent recognition pattern of r56 polypeptide compared to whole cell extracts, the r56 polypeptide is a good candidate vaccine component.

Two strains of either relatively outbred mice (CD1) or an inbred strain (C3H) were immunized, with adjuvant with the r56 polypeptide. At various times after administration of the polypeptide the animals were challenged with live *O. tsutsugamushi*. The protective efficacy of administration of r56 polypeptide is shown in table 4.

TABLE 4

Protection of Mice by Immunization with r56

| Experiment | Strain of mice | Dose/Mouse (adjuvant) | Challenge date post immunization | % Protection |
|---|---|---|---|---|
| I | C3H | 25 μg (incomp. Freunds) | 3 weeks | 100% |
| II | CD1 | 25 μg (Titer Max) | 4 months | 60% |
| III | CD1 | 2 μg (Titer Max) | 4 weeks | 60% |

REFERENCES

1. Amano, K., A. Tamura, N. Ohashi, H. Urakami, S. Kaya, and K. Fukushi. 1987. Deficiency of peptidoglycan and lipopolysaccharide components in *Rickettsia tsutsugamushi*. Infect. Immun. 55:2290–2292.

2. Blanar, M. A., D. Kneller, A. J. Clark, A. E. Karu, F. E. Cohen, R. Langridge, and I. D. Kuntz. 1984. A model for the core structure of the *Escherichia coli* RecA protein. Cold Spring Harb. Symp. Quant. Biol. 49:507–511.
3. Bourgeois, A. L., J. G. Olson, R. C. Fang, J. Huang, C. L. Wang, L. Chow, D. Bechthold, D. T. Dennis, J. C. Coolbaugh, and E. Weiss. 1982. Humoral and cellular responses in scrub typhus patients reflecting primary infection and reinfection with *Rickettsia tsutsugamushi*. Am. J. Trop. Med. Hyg. 31:532–540.
4. Bozeman, F. M., and B. L. Elisberg. 1963. Serological diagnosis of scrub typhus by indirect immunofluorescence. Proc. Soc. Exp. Biol. Med. 112:568–573.
5. Brown, G. W., D. M. Robinson, D. L. Huxsoll, T. S. Ng, K. J. Lim, and G. Sannasey. 1976. Scrub typhus: a common cause of illness in indigenous populations. Trans. R. Soc. Trop. Med. Hyg. 70: 444–448.
6. Brown, G. W., J. P. Saunders, S. Singh, D. L. Huxsoll, and A. Shirai. 1978. Single dose doxycycline therapy for scrub typhus. Trans. R. Soc. Trop. Med. Hyg. 72:412–416.
7. Chang W-H. 1995. Current status of tsutsugamushi disease in Korea. J. Korean Med. Sci. 10:227–238.
8. Ching, W.-M., H. Wang, and G. A. Dasch. 1996. Identification of human antibody epitopes on the 47 kDa, 56 kDa, and 22 kDa protein antigens of *Orientia tsutsugamushi* with synthetic peptides. Amer. J. Trop. Med. Hyg. 55:300. Abstract # 608
9. Cohen, F. E., R. M. Abarbanel, I. D. Kuntz, and R. J. Fletterick. 1983. Secondary structure assignment for α/β proteins by a combinatorial approach. Biochemistry 22:4894–4904.
10. Crum, J. W., S. Hanchalay, and C. Eamsila. 1980. New paper enzyme-linked immunosorbent technique compared with microimmunofluorescence for detection of human serum antibodies to *Rickettsia tsutsugamushi*. J. Clin. Microbiol. 11:584–588.
11. Dasch G. A., S. Halle, and L. Bourgeois. 1979. Sensitive microplate enzyme-linked immunosorbent assay for detection of antibodies against the scrub typhus rickettsia,
12. Dasch. G. A., D. Strickman, G. Watt, and C. Eamsila. 1996. Measuring genetic variability in *Orientia tsutsugamushi* by PCR/RFLP analysis: a new approach to questions about its epidemiology, evolution, and ecology, p. 79–84. In J. Kazar (ed.) Rickettsiae and Rickettsial Diseases. Vth International Symposium. Slovak Academy of Sciences, Bratislava.
13. Dohany A. L., A. Shirai, D. M. Robinson, S. Ram, and D. L. Huxsoll. 1978. Identification and antigenic typing of *Rickettsia tsutsugamushi* in naturally infected chiggers (Acarina: Trombiculidae) by direct immunofluorescence. Am. J. Trop. Med. Hyg. 27:1261–1264.
14. Furuya, Y., Y. Yoshida, T. Katayama, F. Kawamori, S. Yamamoto, N. Ohashi, A. Kamura, and A. Kawamura, Jr. 1991. Specific amplification of *Rickettsia tsutsugamushi* DNA from clinical specimen by polymerase chain reaction. J. Clin Microbiol. 29: 2628–2630.
15. Greenfield, N., and G. D. Fasman. 1969. Computed circular dichroism spectra for the evaluation of protein conformation. Biochemistry 10:4108–4116.
16. Hanson, B. 1985. Identification and partial characterization of *Rickettsia tsutsugamushi* major protein immunogens. Infect. Immun. 50:603–609.
17. Horinouchi, H., K. Murai, A. Okayama, Y. Nagatomo, N. Tachibana, and H. Tsubouchi. 1996. Genotypic idenfication of *Rickettsia tsutsugamushi* by restriction fragment length polymorphism analysis of DNA amplified by the polymerase chain reaction. Am. J. Trop. Med. Hyg. 54:647–651.
18. Kelly, D. J., G. A. Dasch, T. C. Chye, and T. M. Ho. 1994. Detection and characterization of *Rickettsia tsutsugamushi* (Rickettsiales: Rickettsiaceae) in infected *Leptotrombidium* (Leptotrombidium) *fletcheri* chiggers (Acari: Trombiculidae) with the polymerase chain reaction. J. Med. Entomol. 31:691–699.
19. Kelly, D. J., D. Marana, C. Stover, E. Oaks, and M. Carl. Detection of *Rickettsia tsutsugamushi* by gene amplification using polymerase chain reaction techniques. Ann. N. Y. Acad. Sci. 590:564–571.
20. Kelly, D. J., P. W. Wong, E. Gan, and G. E. Lewis, Jr. 1988. Comparative evaluation of the indirect immunoperoxidase test for the serodiagnosis of rickettsial disease. Am. J. Trop. Med. Hyg. 38:400–406.
21. Kim, I-S., S-Y. Seong, S-G. Woo, M-S. Choi, and W-H. Chang. 1993. High-level expression of a 56-kilodalton protein gene (bor56) of *Rickettsia tsutsugamushi* Boryong and its application to enzyme-linked immunosorbent assays. J. Clin. Microbiol. 31:598–605.
22. Kim, I-S., S-Y. Seong, S-G. Woo, M-S. Choi, and W-H. Chang. 1993. Rapid diagnosis of scrub typhus by a passive hemagglutination assay using recombinant 56-kilodalton polypeptide. J. Clin. Microbiol. 31:2057–2060.
23. Moree, M. F., and B. Hanson. 1992. Growth Characteristics and proteins of plaque-purified strains of *Rickettsia tsutsugamushi*. Infect. Immun. 60:3405–3415.
24. Murata, M. Y. Yoshida, M. Osono, N. Ohashi, Oyanagi, H. Urakami, A. Tamura, S. Nogami, H. Tanaka, and A. Kawamura, Jr. 1986. Production and characterization of monoclonal strain-specific antibodies against prototype strains of *Rickettsia tsutsugamushi*. Microbiol. Immunol. 30:599–610.
25. Ohashi, N., Y. Koyama, H. Urakami, M. Fukuhara, A. Tamura, F. Kawamori, S. Yamamoto, S. Kasuya, and K. Yoshimura. 1996. Demonstration of antigenic and genotypic variation in *Orientia tsutsugamushi* which were isolated in Japan, and their classification into type and subtype. Microbiol. Immunol. 40:627–638.
26. Ohashi, N., H. Nashimoto, H. Ikeda, and A. Tamura. 1992. Diversity of immunodominant 56-kDa type-specific antigen (TSA) of *Rickettsia tsutsugamushi*. Sequence and comparative analyses of the genes encoding TSA homologues from four antigenic variants. J. Biol. Chem. 267:12728–12735.
27. Ohashi, N., A. Tamura, M. Ohta, and K. Hayashi. 1989. Purification and partial characterization of a type-specific antigen of *Rickettsia tsutsugamushi*. Infect. Immun. 57:1427–1431.
28. Ohashi, N., A. Tamura, H. Sakurai, and T. Suto. 1988. Immunoblotting analysis of anti-rickettsial antibodies produced in patients of tsutsugamushi disease. Microbiol. Immunol. 32:1085–1092.
29. Ohashi, N., A. Tamura, H. Sakurai, and S. Yamamoto. 1990. Characterization of a new antigenic type, Kuroki, of *Rickettsia tsutsugamushi* isolated from a patient in Japan. J. Clin. Microbiol. 28:2111–2113.
30. Robinson, D. M., G. Brown, E. Gan, and D. L. Huxsoll. 1976. Adaptation of a microimmunofluorescence test to the study of human *Rickettsia tsutsugamushi* antibody. Am. J. Trop. Med. Hyg. 25:900–905.
31. Saunders, J. P., G. W. Brown, A. Shirai, and D. L. Huxsoll. 1980. The longevity of antibody to *Rickettsia*

*tsutsugamushi* in patients with confirmed scrub typhus. Trans. Roy. Soc. Trop. Med. Hyg. 74:253–257.

32. Shirai, A., D. M. Robinson, G. W. Brown, E. Gan, and D. L. Huxsoll. 1979. Antigenic analysis by direct immunofluorescence of 114 isolates of *Rickettsia tsutsugamushi* recovered from febrile patients in rural Malaysia. Japan J Med Sci Biol 32:337–344.
33. Silverman, D. J., and C. L. Wisseman, Jr. 1978. Comparative ultrastructural study on the cell envelopes of *Rickettsia prowazekii, Rickettsia rickettsii*, and *Rickettsia tsutsugamushi*. Infect. Immun. 21(3):1020–1023.
34. Stover, C. K., D. P. Marana, J. M. Carter, B. A. Roe, E. Mardis, and E. V. Oaks. 1990. The 56-kilodalton major protein antigen of *Rickettsia tsutsugamushi*: molecular cloning and sequence analysis of the sta56 gene and precise identification of a strain-specific epitope. Infect. Immun. 58(7):2076–2084.
35. Studier, F. W., and B. A. Moffatt. 1986. Use of bacteriophage T7 RNA polymerase to direct selective high-level expression of cloned genes. J. Mol. Biol. 189:113–130.
36. Sugita, Y., T. Nagatani, K Okuda, Y. Yoshida, and H. Nakajima. 1992. Diagnosis of typhus infection with *Rickettsia tsutsugamushi* by polymerase chain reaction. J. Med. Microbiol. 37:357–360.
37. Suto, T. 1980. Rapid serological diagnosis of tsutsugamushi disease employing the immuno-peroxidase reaction with cell cultured rickettsia. Clin. Virol. 8:425–
38. Suwanabun, N., C. Chouriyagune, C. Eamsila, P. Watcharapichat, G. A. Dasch, R. S. Howard, and D. J. Kelly. 1997. Evaluation of an enzyme-linked immunosorbent assay in Thai scrub typhus patients. Am. J. Trop. Med. Hyg. 56:38–43
39. Tamura, A., N. Ohashi, Y. Koyama, M. Fukuhara, F. Kawamori, M. Otsuru, P-F. Wu, and S-Y. Lin. 1997. Characterization of *Orientia tsutsugamushi* isolated in Taiwan by immunofluorescence and restriction fragment length polymorphism analyses. FEMS Microbiol. Lett. 150:225–231.
40. Urakami, H., S. Yamamoto, T. Tsuruhara, N. Ohashi, and A. Tamura. 1989. Serodiagnosis of scrub typhus with antigens immobilized on nitrocellulose sheet. J. Clin. Microbiol. 27:1841–1846.
41. Weddle, J. R., T. C. Chan, K. Thompson, H. Paxton, D. J. Kelly, G. Dasch, and D. Strickman. 1995. Effectiveness of a dot-blot immunoassay of anti-*Rickettsia tsutsugamushi* antibodies for serologic analysis of scrub typhus. Am. J. Trop. Med. Hyg. 53:43–46.
42. Yamamoto, S., N. Kawabata, A. Tamura, H. Urakami, N. Ohashi, M. Murata, Y. Yoshida, and A. Kawamura, Jr. 1986. Immunological properties of *Rickettsia tsutsugamushi*, Kawasaki strain, isolated from a patient in Kyushu. Microbiol. Immunol. 30:611–620.
43. Yamamoto, S., and Y. Minamishima. 1982. Serodiagnosis of tsutsugamushi fever (scrub typhus) by the indirect immunoperoxidase technique. J. Clin. Microbiol. 15:1128–1132.

Obviously, many modifications and variations of the present invention are possible in light of the above teachings. It is therefore to be understood that, within the scope of the appended claims, the invention may be practiced otherwise than as specifically described.

What is claimed is:

1. An assay for detecting antibody to scrub typhus using scrub typhus antigen comprising:

(a) Obtaining a sample suspected of containing said antibody from a subject;

(b) Exposing the sample to said antigen comprising a polypeptide of SEQ ID NO.:1, said polypeptide being a refolded expression product of a truncated non-fusion 56 kDa gene from *Orientia tsutsugamushi;*

(c) Incubating said sample, wherein said antibody binds said polypeptide forming a complex;

(d) Binding a detectable label to said complex wherein a detectable signal is produced;

(e) Detecting the signal, wherein the signal indicates the presence of said antibody.

2. An assay, according to claim 1 wherein the polypeptide is an antigen for the detection of prior exposure to scrub typhus in subjects.

3. An assay, according to claim 1 wherein the immunoassay format is enzyme-linked immunosorbant assay (ELISA).

4. An assay, according to claim 1 wherein the immunoassay format is indirect immunofluorescent (IIP) assay.

5. An assay, according to claim 1, wherein the immunoassay format is a dot-blot assay.

6. An assay, according to claim 1, wherein the immunoassay format is a rapid flow assay.

7. An assay, according to claim 1, wherein the immunoassay is a paramagnetic beads assay.

8. An assay, according to claim 1, wherein the immunoassay is a fluorescence bead assay.

9. An assay, according to claim 1, wherein said detectable label is colloidal gold.

10. An assay for detecting scrub typhus specific 56 kDa antigen using scrub typhus antibody comprising:

(a) Obtaining a sample suspected of containing said antigen from a subject said antigen comprising a polypeptide of SEQ ID NO.:1;

(b) Exposing the sample to an antibody against said polypeptide;

(c) Incubating said sample, wherein said antibody binds said antigen forming a complex;

(d) Binding a detectable label to said complex wherein a detectable signal is produced;

(e) Detecting the signal, wherein the signal indicates the presence of said antigen.

11. An assay, according to claim 10, wherein the polypeptide is an antigen for the detection of prior exposure to scrub typhus in subjects.

12. An assay, according to claim 10, wherein the immunoassay format is enzyme-linked immunosorbant assay.

13. An assay, according to claim 10, wherein the immunoassay format is indirect immunofluorescent assay.

14. An assay, according to claim 10, wherein the immunoassay format is a dot-blot assay.

* * * * *